US005662597A

United States Patent [19]
Chitwood

[11] Patent Number: 5,662,597
[45] Date of Patent: Sep. 2, 1997

[54] GRAVITY TRACTION DEVICE

[75] Inventor: Ralph M. Chitwood, Kalispell, Mont.

[73] Assignee: Glacier Cross, Inc., Kalispell, Mont.

[21] Appl. No.: 516,007

[22] Filed: Aug. 16, 1995

Related U.S. Application Data

[63] Continuation-in-part of Ser. No. 327,021, Oct. 21, 1994, Pat. No. 5,569,175, which is a continuation-in-part of Ser. No. 303,691, Sep. 9, 1994, Pat. No. 5,454,781, which is a continuation-in-part of Ser. No. 120,602, Sep. 13, 1993, Pat. No. 5,441,479.

[51] Int. Cl.$^6$ ........................................ A61F 5/00
[52] U.S. Cl. ..................... 602/32; 602/36; 606/241; 601/24
[58] Field of Search ................ 602/32–36; 606/241, 606/242, 244; 482/96, 142, 907; 601/23, 24, 39; 5/610, 636, 637; D24/183, 184; 128/845, 857

[56] References Cited

U.S. PATENT DOCUMENTS

| | | |
|---|---|---|
| 309,678 | 12/1884 | Aubin ............................ 606/241 |
| D. 344,135 | 2/1994 | Price . |
| 2,638,091 | 5/1953 | Varco . |
| 3,060,925 | 10/1962 | Honsaker et al. ............... 606/242 |
| 3,124,126 | 3/1964 | Spinus ............................ 606/242 |
| 3,343,532 | 9/1967 | Zumaglini . |
| 3,570,479 | 3/1971 | Horn . |
| 3,621,839 | 11/1971 | Barthe ............................ 602/32 |
| 4,103,681 | 8/1978 | Shanley . |
| 4,166,459 | 9/1979 | Nightingale .................. 602/32 |
| 4,204,529 | 5/1980 | Cochrane . |
| 4,473,912 | 10/1984 | Scheidel et al. . |
| 4,508,109 | 4/1985 | Saunders . |
| 4,524,763 | 6/1985 | Eberling, Jr. .................. 606/241 |
| 4,534,341 | 8/1985 | Bart et al. ..................... 606/241 |
| 4,535,762 | 8/1985 | Natchev ........................ 606/244 |
| 4,627,422 | 12/1986 | Bates . |
| 4,700,696 | 10/1987 | Schoffstall . |
| 4,732,144 | 3/1988 | Cunanan . |
| 4,736,736 | 4/1988 | Moers et al. . |
| 4,771,493 | 9/1988 | Park . |
| 4,805,603 | 2/1989 | Cumberland . |
| 4,832,007 | 5/1989 | Davis, Jr. et al. . |
| 4,890,604 | 1/1990 | Nelson ........................... 602/32 |
| 5,020,520 | 6/1991 | Lawlis . |
| 5,052,378 | 10/1991 | Chitwood . |
| 5,067,483 | 11/1991 | Freed . |
| 5,074,287 | 12/1991 | Avitt . |
| 5,100,131 | 3/1992 | Fong . |
| 5,109,835 | 5/1992 | McDonald et al. ............. 606/241 |
| 5,192,306 | 3/1993 | Scott et al. . |
| 5,382,226 | 1/1995 | Graham . |
| 5,409,452 | 4/1995 | Aversano . |

*Primary Examiner*—Jeanne M. Clark
*Attorney, Agent, or Firm*—Thomas R. Vigil

[57] ABSTRACT

The gravity traction device comprises an inclined platform or table having an upper inclined surface for supporting a user's upper body or torso and a generally U-shaped, head receiving portion mounted to the platform adjacent an upper end thereof and having contoured surfaces for receiving and supporting a user's head and neck and a ridge with an adjacent lift surface for engaging against the occipital bone of the user's head received in the head receiving portion.

4 Claims, 4 Drawing Sheets

GRAVITY TRACTION DEVICE

CROSS REFERENCE TO RELATED APPLICATIONS

This application is a continuation-in-part of U.S. application Ser. No. 08/327,021 filed on Oct. 21, 1994, now U.S. Pat. No. 5,569,175 which is a continuation-in-part of U.S. application Ser. No. 08/303,691 filed on Sep. 9, 1994, now U.S. Pat. No. 5,454,781, issued Oct. 2, 1995, which is a continuation-in-part of U.S. application Ser. No. 08/120,602 filed on Sep. 13, 1993, now U.S. Pat. No. 5,441,479, issued Aug. 15, 1995.

BACKGROUND OF THE INVENTION

1. Field of the Invention

The present invention relates to a gravity traction device which includes an inclined platform or table that has an upper inclined surface for supporting a person's upper body or torso and head and neck support structure attached to the platform adjacent an upper end thereof. The head and neck support structure includes a generally U-shaped head receiving portion fixed to the platform and having contoured surfaces for receiving a patient's head and neck and a ridge on the head receiving portion for engaging against the occipital bone of a patient's head received in the head receiving portion.

2. Description of the related art including information disclosed under 37 CFR §§1.97–1.99

Heretofore it has been proposed in the Cumberland U.S. Pat. No. 4,805,603 to provide a cervical traction/stretch and neck curve support device comprising a head/neck/shoulder support unit having a vertical slot in the region corresponding to the cervical area. The slot separates the unit into a first section and a second section. The upper surfaces of each of the sections is shaped to receive the head, neck and shoulders of a reclining person. An inflatable air sack is located within the unit between the first and second sections and a hand operated bulb type air pump is provided for pumping up the air sack.

Also in applicant's earlier application, Ser. No. 08/120, 602, now U.S. Pat. No. 5,441,479, issued Aug. 15, 1995, there is disclosed a cervical traction/stretch and neck curve support device comprising a body including a shoulder portion, a head portion and a bellows which extends substantially across the width and height of the body between and connected to the head portion and to the shoulder portion and acting against and between substantially the full inner end surface of the head portion and the full inner end surface of the shoulder portion. The bellows, the shoulder portion and the head portion have aligned U-shaped openings therein adapted to receive a patient's neck. A hand operated air pump is provided for pumping air into the bellows and for releasing air from the bellows.

The gravity traction device of the present invention is designed to use gravity acting on a patient's body and tending to pull the patient's body downwardly along the upper inclined surface of an inclined platform or table to create traction on the patient's neck received in the head receiving portion.

Other analogous and non-analogous traction devices are disclosed in the following U.S. Patents:

| U.S. PAT. NO. | Patentee |
| --- | --- |
| 2,638,091 | Varco |
| 3,343,532 | Zumaglini |
| 3,570,479 | Horn |
| 4,103,681 | Shanley |
| 4,204,529 | Cochrane |
| 4,473,912 | Scheidel et al. |
| 4,508,109 | Saunders |
| 4,627,422 | Bates |
| 4,700,696 | Schoffstall |
| 4,732,144 | Cunanan |
| 4,736,736 | Moers et al. |
| 4,771,493 | Park |
| 4,805,603 | Cumberland |
| 4,832,007 | Davis, Jr. et al. |
| 5,020,520 | Lawlis |
| 5,067,483 | Freed |
| 5,052,378 | Chitwood |
| 5,074,287 | Avitt |
| 5,100,131 | Fong |
| 5,192,306 | Scott et al |
| 5,382,226 | Graham |
| 5,409,452 | Aversano |
| Des.344,135 | Price |

SUMMARY OF THE INVENTION

According to the present invention there is provided a gravity traction device comprising: an inclined platform or table which is inclined to the horizontal at an angle of between 10° and 80° and which has an upper inclined surface for supporting a user's upper body or torso; a generally U-shaped, head receiving member mounted to the platform adjacent an upper end of the platform and having a top, a bottom, a right side, a left side, an outer, upper end, an inner end surface and a generally U shaped surface extending downwardly from the top and outwardly from the inner end surface of the head receiving member and having a contoured head receiving surface for receiving and supporting a user's head and neck, the contoured surface including a ridge extending downwardly from a location below the top on either side of the U-shaped surface and an adjacent lift surface, the contoured head receiving surface of the head receiving member extending downwardly to the bottom of the head receiving member within the head receiving member and the head receiving member at the bottom has a U-shaped notch extending inwardly from the outer, upper end whereby a patient's head can rest partially on the contoured head receiving surface and partially on the platform upon which the head receiving member is positioned, the ridge being pronounced at the location of a junction between the U-shaped surface and the contoured head receiving surface and each lift surface extending from the ridge laterally toward one of the sides and toward the outer, upper end of the head receiving member for engaging against the occipital bone of the user's head received in the head receiving member; and, a head strap releasably connectable to the head receiving member and about a user's or patient's head received in the head receiving member. for engaging against the occipital bone of the user's head received in the head receiving portion.

DESCRIPTION OF THE PREFERRED EMBODIMENT

Figure 1:
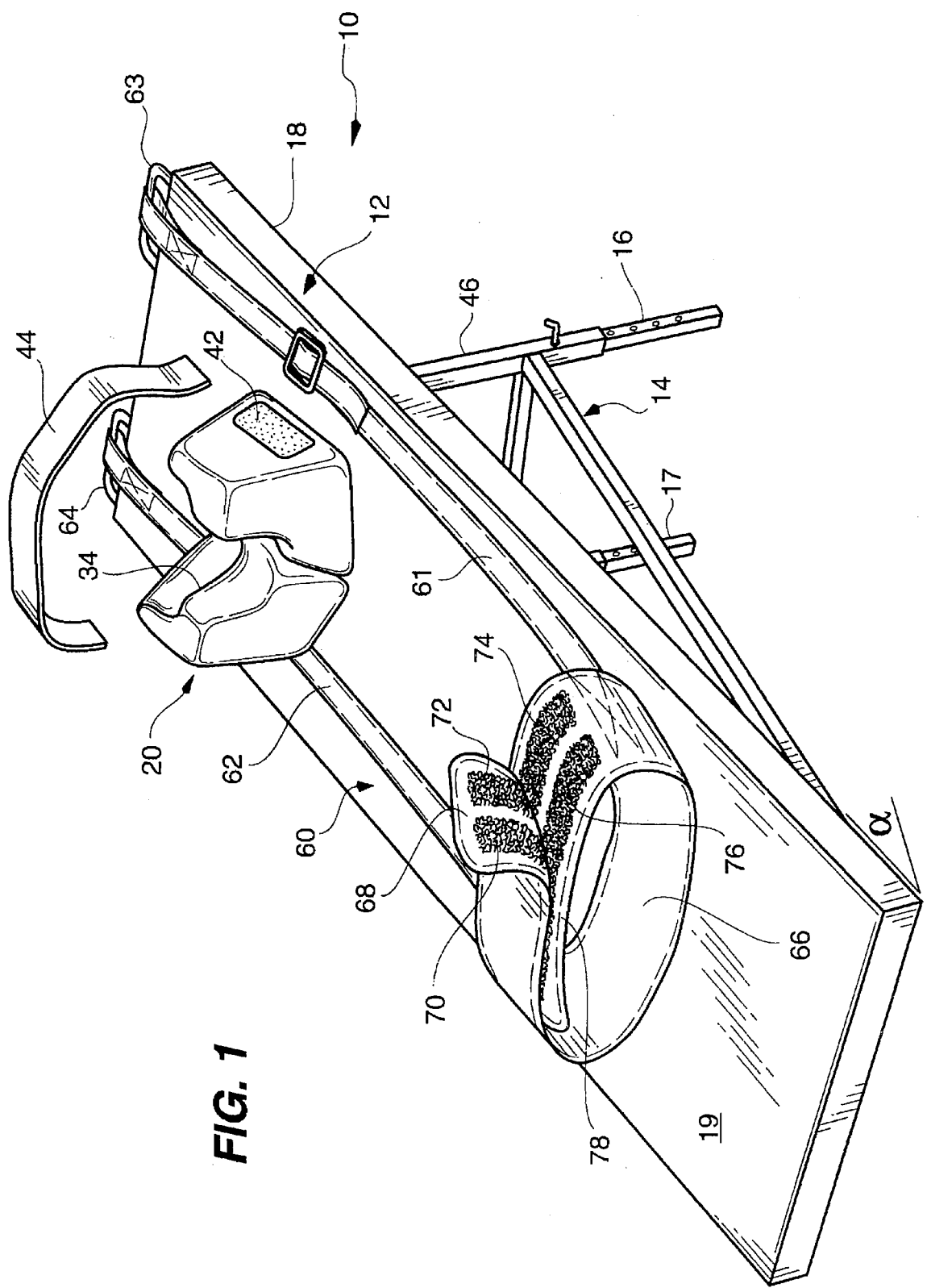
FIG. 1 is an upper perspective view of the gravity traction device constructed according to the teachings of the present invention.

Referring now to the drawings in greater detail there is illustrated in FIG. 1 a gravity traction device 10 constructed according to the teachings of the present invention. The device 10 includes a platform or table 12 mounted on a framework 14 having a pair of adjustable legs 16,17 at, and beneath, an upper end 18 of the table 12 for adjusting an angle, α, of incline of an upper flat surface 19 of the table 12 relative to a supporting floor surface. The angle, α, can be between 10° and 80°, 30° to 60° being preferred.

The gravity traction device 10 also includes a head receiving member or portion 20 mounted to the table 12. In this respect, a bottom facing surface (not shown) of the head receiving portion 20 is secured, such as by an adhesive or by hook and loop type fastening structure of the type sold under the trademark VELCRO®, to the upper surface 19 of the table 12.

Details on the construction of the head receiving portion 20 are found in co-pending application Ser. No. 08/120,602, now U.S. Pat. No. 5,441,055, of which this application is a continuation-in-part and the disclosure of which is incorporated herein by reference.

Important features of the head receiving portion 20 are described in the parent application and are generally described below.

As disclosed in and U.S. Ser. No. 08/120,602 the head portion has a top, a bottom, a left side, a right side, an outer end, a U-shaped surface which extends downwardly from the top and outwardly from an inner end surface of the head portion and a contoured curved head receiving surface which extends outwardly from the U-shaped surface of the head portion and downwardly to the outer end and to the bottom of the head portion, all of the U-shaped surfaces in the middle, bight area of the U-shaped openings conforming generally to the natural cervical curve of a patient's neck which is received therein.

The head receiving surface of the head portion extends downwardly to the bottom of the head portion within the head portion and the head portion at the bottom has a U-shaped notch extending inwardly from the outer end whereby a patient's head can rest partially on the head receiving surface and partially on a planar surface upon which the body of the cervical traction device is positioned.

The head portion has a shoulder between the generally U-shaped surface and the head receiving surface in the area on each side of the U-shaped space above the bight portion and below the top of the head portion for engaging and exerting pressure against the occipital bone on each side of a patient's head.

With particular reference to FIGS. 3–7, the head receiving portion 20 has a generally arcuate or semi-cylindrical U-shaped surface 24 having a portion 26 at the center of the head receiving portion 20 to fit and support the cervical curve of a patient's neck and has a head receiving surface 28 having a center portion 30 that curves inwardly for mating with the cervical curve.

The U-shaped surface 24 extends toward the outer or upper end 32 of the head receiving portion 12 a distance approximately ¾ of an inch to one inch and forms a ridge or shoulder 34 (FIG. 3) on opposite sides of the U-shaped curved surface 24 but not at the center of the U-shaped curved surface 24.

Part way up either side of the U-shaped surface the ridge or shoulder 34 is pronounced and is located at the junction between the U-shaped surface 24 and the head receiving surface 28. The ridge or shoulder 34 at this location is adapted to bear against the occipital bone and defines in the head receiving surface 28 an occipital-cervical pressure or lift surface 36 just outwardly of the ridge or shoulder 34.

This ridge or shoulder 34 and the adjacent pressure or lift surface 36 of the head receiving surface 28 enables the head receiving portion 20 to apply pressure at the region of the occipital bone of a patient on each side of the neck. It is believed that this pressure on the occipital bone applied with the gravity traction device 10 of the present invention also can alleviate or relieve headache pain.

Most cervical injuries to patients involve the loss of the natural cervical curve forming a so-called military neck or straight neck syndrome. This creates stress on the upper thoracic muscles, as these muscles are forced to hold the head upright. When the natural curve is in place, the head weight is distributed throughout the skeletal system. The head receiving portion 20 of the gravity traction device 10 is constructed so that the patient's cervical curve is supported to relieve upper thoracic muscles from unnatural stress with the upper surface 19 of the table 12 inclined between 10° and 80° to the horizontal, so that gravity, acting on the patient's or user's body will cause the patient's or user's head, in the area of the occipital bone to bear against the ridge 34 and lift surface 36.

Figure 2:
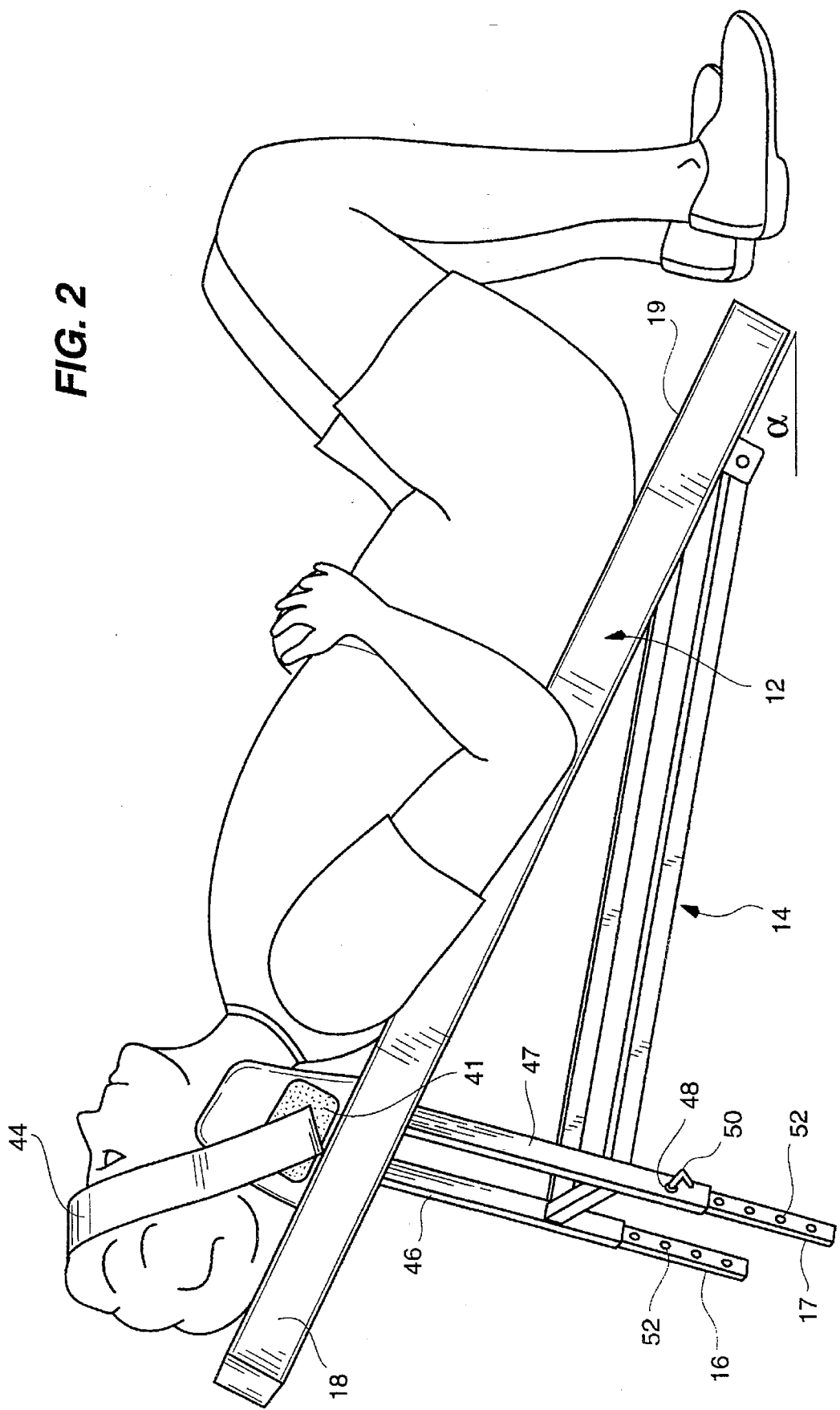
FIG. 2 is a side perspective view of a modified gravity traction device constructed according to the teachings of the present invention and having a patient or user lying thereon.
Figure 3:
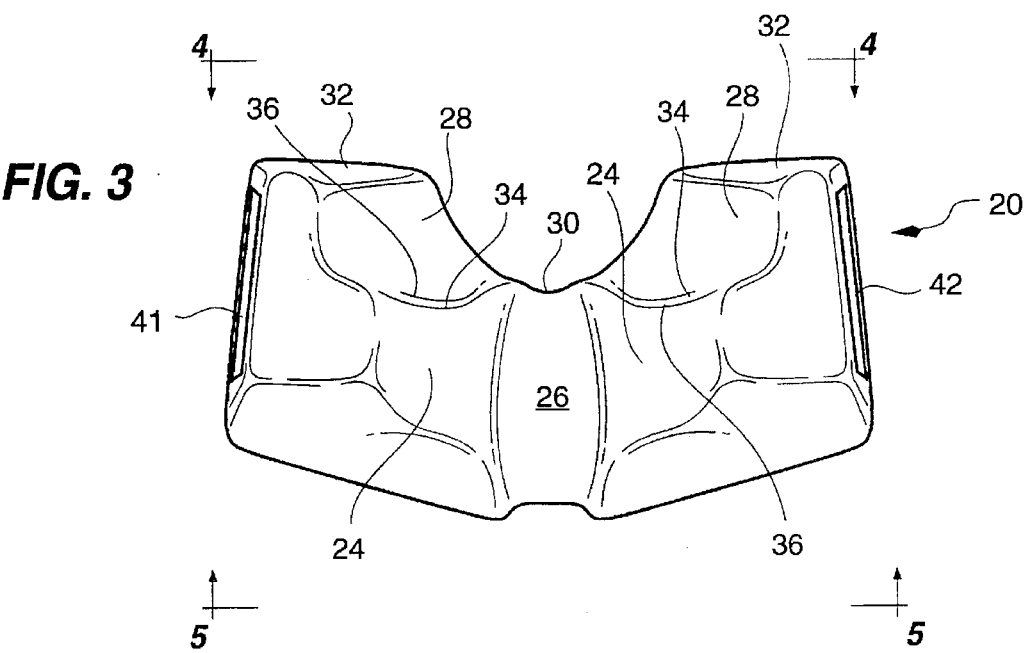
FIG. 3 is a top view of the head receiving portion of the gravity traction device shown in FIG. 1.
Figure 4:
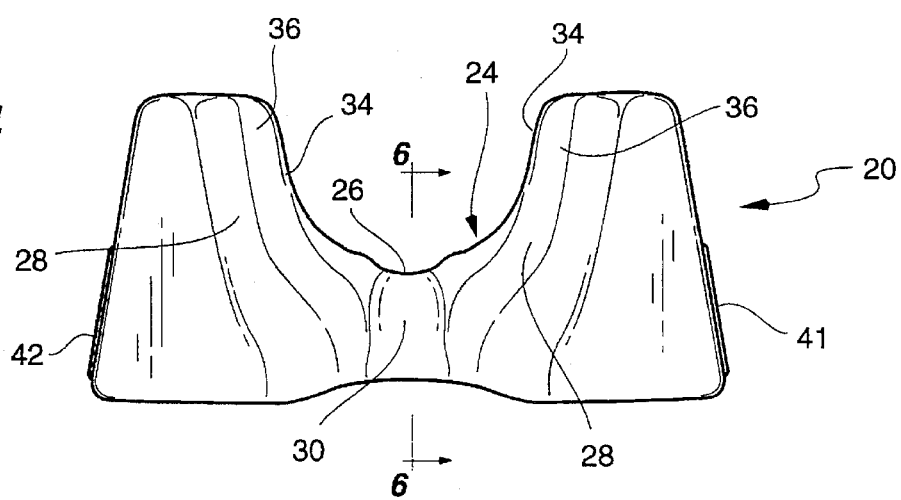
FIG. 4 is an upper end view of the head receiving portion shown in FIG. 3.
Figure 5:
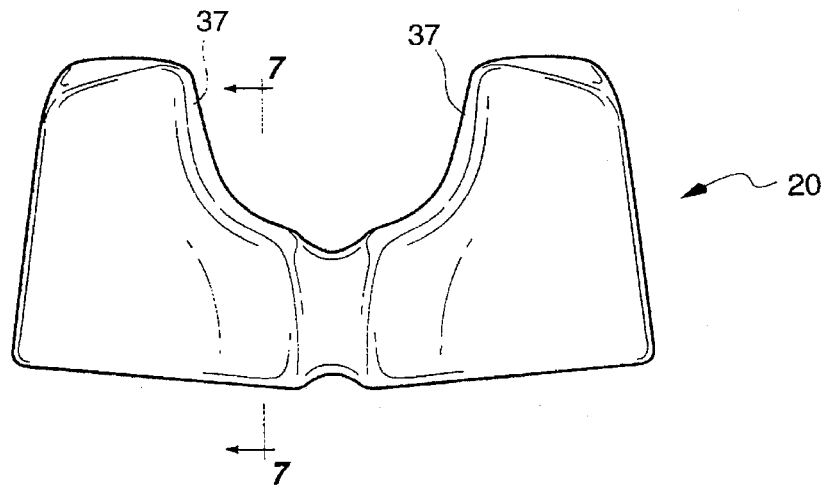
FIG. 5 is a lower end view of the head receiving portion shown in FIG. 3.
Figure 6:
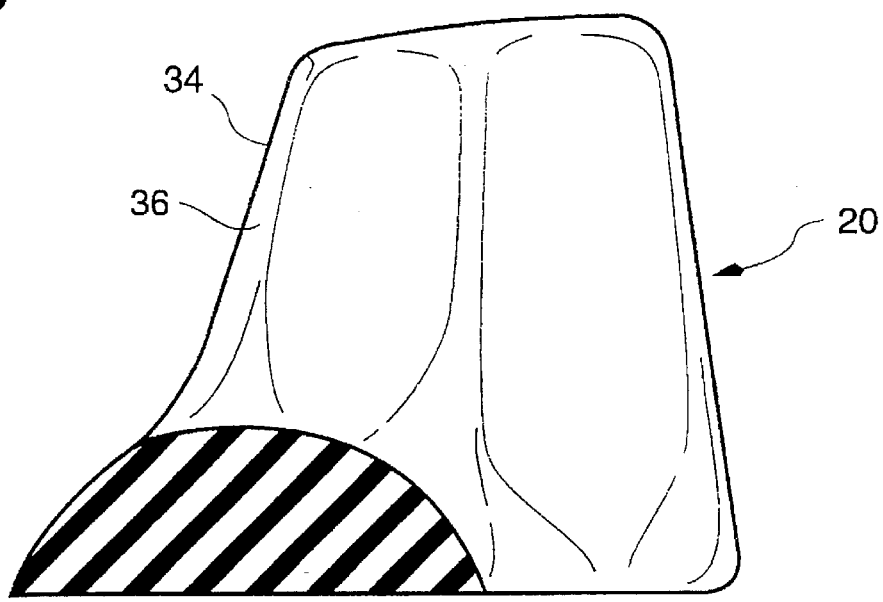
FIG. 6 is a generally vertical sectional view of the head receiving portion shown in FIG. 4 and is taken along line 6—6 of FIG. 4.
Figure 7:
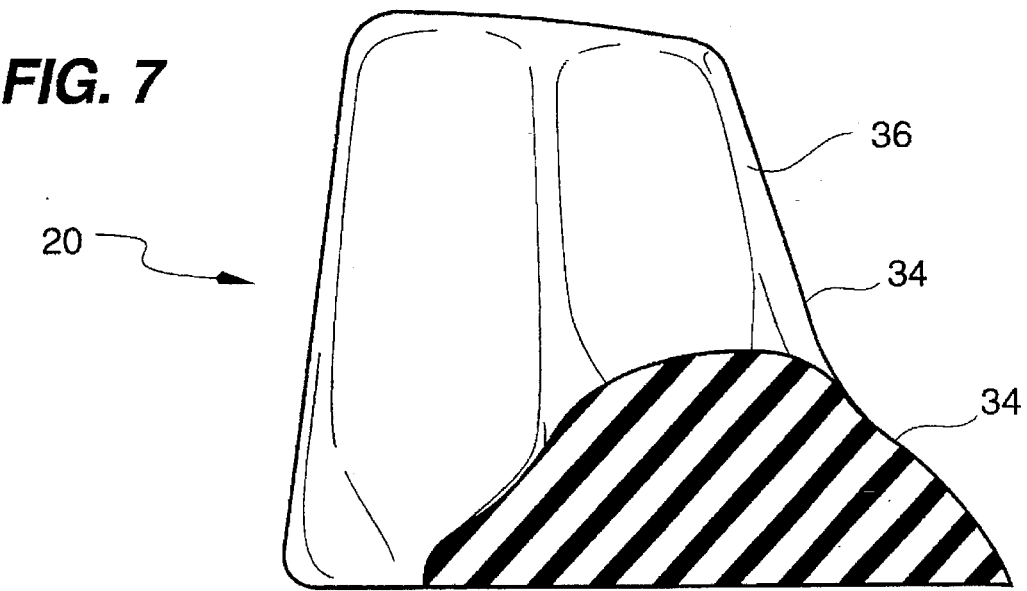
FIG. 7 is a generally vertical sectional view of the head receiving portion shown in FIG. 5 and is taken along line 7—7 of FIG. 5.

Referring again to FIGS. 1–3, the head receiving portion 12 has on either side thereof, loop and hook type fastening structure 41,42 of the type sold under the trademark VELCRO® and a head strap 44 which is adapted to be received over a patient's head and secured to the fastening structure 41,42.

The head strap 44 holds the patient properly and securely for the best benefit of occipital lift and immobilizes the patient for accuracy in treatment.

Referring again to FIGS. 1 and 2, the framework 14 includes tubular leg portions 46,47 (FIG. 2) which receive the adjustable legs 16 and 17, respectively. The lower end of each tubular leg portion 46 and 47 has a side hole 48 for receiving a pin 50 which also is received in one of a plurality of holes 52 in each of the legs 16 and 17 for adjusting the angle α to vary the angle of inclination between 10° and 80° and preferably between 30° and 60°.

It will be understood that other forms of leg adjustment mechanisms can be utilized for adjusting the height of the upper end 18 of the table 12.

Also if desired, a body holding strap assembly 60 can be provided as shown in FIG. 1. The strap assembly 60 includes two straps 61,62 to two bales or loops 63,64 mounted to the upper end of the table 12. The straps 61,62 are adjustable and connected at the lower end to a waist or torso belt 66 which has on an inner surface 68 at one end 70 loop and hook type fastening material 72 of the type sold under the trademark Velcro® for attachment to loop and hook type fastening material 74 of the type sold under the trademark Velcro® on the outer surface 76 at the other end 78 of the belt 66.

The strap assembly 60 can be used to limit the amount of gravity force exerted by the user's or patient's head against the ridge or shoulder 34 and the adjacent lift surface 36 of the head receiving portion 20. Also, the amount of force exerted against the user's or patient's head is controlled by the angle, α, of inclination of the upper surface 19 of the table 12 to the horizontal. Empirical tests have shown that an angle α between 45° and 75° typically produces enough gravity force from the user's/patient's body on the occipital bone at the back of the head of the patient or user to provide adequate stretching of the cervical area of the neck.

From the foregoing description, it will be apparent that the gravity traction device 10 of the present invention has a number of advantages, some of which have been described above and others of which are inherent in the invention.

Also from the foregoing description, it will be apparent that modifications can be made to the gravity traction device 10 of the present invention without departing from the teachings of the invention.

Accordingly, the scope of the invention is only to be limited as necessitated by the accompanying claims.

I claim:

1. A gravity traction device comprising: an inclined platform or table which is inclined to the horizontal at an angle of between 10° and 80° and which has an upper inclined surface for supporting a user's upper body or torso; a generally U-shaped, head receiving member mounted to said platform adjacent an upper end of said platform and having a top, a bottom, a right side, a left side, an outer, upper end, an inner end surface and a generally U shaped surface extending downwardly from said top and outwardly from said inner end surface of said head receiving member and having a contoured head receiving surface for receiving and supporting a user's head and neck, said contoured surface including a ridge extending downwardly from a location below said top on either side of said U-shaped surface and an adjacent lift surface, said contoured head receiving surface of said head receiving member extending downwardly to said bottom of said head receiving member within said head receiving member and said head receiving member at said bottom has a U-shaped notch extending inwardly from said outer, upper end whereby a patient's head can rest partially on said contoured head receiving surface and partially on said platform upon which said head receiving member is positioned, said ridge being pronounced at the location of a junction between said U-shaped surface and said contoured head receiving surface and each lift surface extending from said ridge laterally toward one of said sides and toward said outer, upper end of said head receiving member for engaging against the occipital bone of the user's head received in said head receiving member; and, a head strap releasably connectable to said head receiving member and about a user's or patient's head received in said head receiving member.

2. The gravity traction device of claim 1 wherein said table is inclined to the horizontal at an angle of between 30° and 60°.

3. The gravity traction device of claim 1 wherein said table is inclined to the horizontal at an angle of between 45° and 75°.

4. The gravity traction device of claim 1 further comprising a strap assembly including a pair of straps secured at one end to said upper end of said table and a waist or torso belt secured to the other end of said straps.

* * * * *